(12) United States Patent
Dürst et al.

(10) Patent No.: US 8,575,326 B2
(45) Date of Patent: Nov. 5, 2013

(54) METHOD FOR EARLY DIAGNOSIS OF CARCINOMAS OF THE ANOGENITAL TRACT

(75) Inventors: Matthias Dürst, Jena (DE); Alfred Hansel, Jena (DE); Daniel Steinbach, Lichtentanne (DE)

(73) Assignee: Oncgnostics GmbH, Jena (DE)

( * ) Notice: Subject to any disclaimer, the term of this patent is extended or adjusted under 35 U.S.C. 154(b) by 0 days.

(21) Appl. No.: 13/496,812

(22) PCT Filed: Sep. 17, 2010

(86) PCT No.: PCT/EP2010/005735
§ 371 (c)(1),
(2), (4) Date: Apr. 20, 2012

(87) PCT Pub. No.: WO2011/032721
PCT Pub. Date: Mar. 24, 2011

(65) Prior Publication Data
US 2012/0208180 A1 Aug. 16, 2012

(30) Foreign Application Priority Data
Sep. 18, 2009 (EP) .................................. 09011941

(51) Int. Cl.
*C07H 21/04* (2006.01)
*C12Q 1/68* (2006.01)
*C12P 19/34* (2006.01)

(52) U.S. Cl.
USPC .................... 536/24.33; 536/23.1; 536/24.31; 435/91.2; 435/6.12

(58) Field of Classification Search
None
See application file for complete search history.

(56) References Cited

U.S. PATENT DOCUMENTS

| 2006/0019256 A1* | 1/2006 | Clarke et al. | 435/6 |
| 2007/0026393 A1* | 2/2007 | Berlin et al. | 435/6 |
| 2007/0105105 A1* | 5/2007 | Clelland et al. | 435/6 |

OTHER PUBLICATIONS

Fraga et al. (DNA Methylation: A Profile of Methods and Applications, BioTechniques 33:632-649 (Sep. 2002).*
Wang et al. (Identification of Novel Methylation Markers in Cervical Cancer Using Restriction Landmark Genomic Scanning, Cancer Res 2008; 68: (7).Apr. 1, 2008).*
Cuzick et al., "Overview of the European and North American studies on HPV testing in primary cervical cancer screening." *Int J Cancer*, 2006, vol. 119(5), pp. 1095-1101.
Esteller, "Epigenetic gene silencing in cancer: the DNA hypermethylome." *Hum Mol Genet*, 2007, vol. 16, pp. R50-59.
Jacobs et al., "Group-specific differentiation between high-and low-risk human papillomavirus genotypes by general primer-medicated PCR and two cocktails of oligonucleotide probes," *J Clin Microbiol*, 1995, vol. 33(4), pp. 901-905.
Shames et al., "Methods for detecting DNA methylation in tumors: from bench to bedside."*Cancer Lett.*, 2007, vol. 251(2), pp. 187-198.
Yu, "A novel set of DNA methylation markers in urine sediments for sensitive/specific detection of bladder cancer." *Clin Cancer Res.*, vol. 13(24), pp. 7296-7304.
Wentzensen et al., "Utility of methylation markers in cervical cancer early detection: appraisal of the state-of-the science." *Gynecologic Oncology*, 2009, vol. 112, pp. 293-292.
Huang et al., "Abstract #50, 99th AACR Annual Meeting", Apr. 12-16, 2008, San Diego, CA.
Wang et al., "Identification of novel methylation markers in cervical cancer using restriction landmark genomic scanning." *Cancer Research*, 2008, vol. 68(7), pp. 2489-2497.
Huang et al., "Hypermethylation of CIDEA and RXFP3 as potential epigenetic markers for endometrial cancer", *Proceedings of the American Association for Cancer Research Annual Meeting*, 2008, vol. 49, pp. 12.
Ausch et al., "Comparative analysis of PCR-based biomarker assay methods for colorectal polyp detection from fecal DNA", *Clinical Chemistry*, 2009, vol. 55(8), pp. 1559-1563.
Mueller et al., "A DNA methylation pattern similar to normal tissue is associated with better prognosis in human cervical cancer", *Cancer Letters*, 2004, vol. 209(2), pp. 231-236.
International Search Report mailed Dec. 22, 2010 for the corresponding PCT Application No. PCT/EP2010/005735.

* cited by examiner

*Primary Examiner* — Christopher M Babic
*Assistant Examiner* — Aaron Priest
(74) *Attorney, Agent, or Firm* — Leason Ellis LLP.

(57) ABSTRACT

A method for the early diagnosis of carcinomas of the anogenital tract, preferably of the cervical carcinoma, and the preliminary stages thereof is described. The method is based on the determination of the methylation status of segments of the gene regions of ASTN1 (astrotactin 1) and ZNF671 (zinc finger protein 671, transcription factor). A DNA methylation in the promoter region or the 5'-region of these genes is indicative for carcinomas of the anogenital tract or severe preliminary stages thereof. The present invention also relates to kits which permit the conduction of the diagnostic method according to the invention.

20 Claims, 2 Drawing Sheets

```
                            SEQUENCE LISTING

<160> NUMBER OF SEQ ID NOS: 20

<210> SEQ ID NO 1
<211> LENGTH: 21
<212> TYPE: DNA
<213> ORGANISM: artificial sequence
<220> FEATURE:
<223> OTHER INFORMATION: primer ASTN1_F

<400> SEQUENCE: 1
cgtaagcgtt gttagcgtag c                                              21

<210> SEQ ID NO 2
<211> LENGTH: 21
<212> TYPE: DNA
<213> ORGANISM: artificial sequence
<220> FEATURE:
<223> OTHER INFORMATION: primer ASTN1_R

<400> SEQUENCE: 2
cgcgaaatcg aaacgaaaac g                                              21

<210> SEQ ID NO 3
<211> LENGTH: 21
<212> TYPE: DNA
<213> ORGANISM: artificial sequence
<220> FEATURE:
<223> OTHER INFORMATION: primer DLX1_F

<400> SEQUENCE: 3
tatcgggatt cgcgtttgta c                                              21

<210> SEQ ID NO 4
<211> LENGTH: 23
<212> TYPE: DNA
<213> ORGANISM: artificial sequence
<220> FEATURE:
<223> OTHER INFORMATION: primer DLX1_R

<400> SEQUENCE: 4
cgaccgaact aaaactcaac tcg                                            23

<210> SEQ ID NO 5
<211> LENGTH: 18
<212> TYPE: DNA
<213> ORGANISM: artificial sequence
<220> FEATURE:
<223> OTHER INFORMATION: primer EDIL3_F
```

```
<400> SEQUENCE: 5
gttttcggcg gttcgttc                                           18

<210> SEQ ID NO 6
<211> LENGTH: 18
<212> TYPE: DNA
<213> ORGANISM: artificial sequence
<220> FEATURE:
<223> OTHER INFORMATION: primer EDIL3_R

<400> SEQUENCE: 6
cgaacgctcg actatcgc                                           18

<210> SEQ ID NO 7
<211> LENGTH: 22
<212> TYPE: DNA
<213> ORGANISM: artificial sequence
<220> FEATURE:
<223> OTHER INFORMATION: primer ITGA4_F

<400> SEQUENCE: 7
cgaattcggt tttcgaaggg tc                                      22

<210> SEQ ID NO 8
<211> LENGTH: 22
<212> TYPE: DNA
<213> ORGANISM: artificial sequence
<220> FEATURE:
<223> OTHER INFORMATION: primer ITGA4_R

<400> SEQUENCE: 8
cacgaccgaa taccgaaca ac                                       22

<210> SEQ ID NO 9
<211> LENGTH: 21
<212> TYPE: DNA
<213> ORGANISM: artificial sequence
<220> FEATURE:
<223> OTHER INFORMATION: primer RXFP3

<400> SEQUENCE: 9
atttcggaaa gcgttttcg c                                        21

<210> SEQ ID NO 10
<211> LENGTH: 21
<212> TYPE: DNA
<213> ORGANISM: artificial sequence
<220> FEATURE:
<223> OTHER INFORMATION: primer RXFP3_R

<400> SEQUENCE: 10
ctacgtctct ccgcgattat c                                       21

<210> SEQ ID NO 11
<211> LENGTH: 23
<212> TYPE: DNA
<213> ORGANISM: artificial sequence
<220> FEATURE:
<223> OTHER INFORMATION: primer ZNF671_F

<400> SEQUENCE: 11
cggaggacgt agtatttatt cgc                                     23

<210> SEQ ID NO 12
<211> LENGTH: 20
```

```
<212> TYPE: DNA
<213> ORGANISM: artificial sequence
<220> FEATURE:
<223> OTHER INFORMATION: primer ZNF671_R

<400> SEQUENCE: 12
ctacgtcccc gatcgaaacg                                               20

<210> SEQ ID NO 13
<211> LENGTH: 28
<212> TYPE: DNA
<213> ORGANISM: artificial sequence
<220> FEATURE:
<223> OTHER INFORMATION: probe ASTN1

<400> SEQUENCE: 13
gtaattcgtt tgtttcgtaa gttgttcg                                      28

<210> SEQ ID NO 14
<211> LENGTH: 27
<212> TYPE: DNA
<213> ORGANISM: artificial sequence
<220> FEATURE:
<223> OTHER INFORMATION: probe DLX1

<400> SEQUENCE: 14
cgtaaacgtt agctgttctg gaaaccg                                       27

<210> SEQ ID NO 15
<211> LENGTH: 23
<212> TYPE: DNA
<213> ORGANISM: artificial sequence
<220> FEATURE:
<223> OTHER INFORMATION: probe EDIL3

<400> SEQUENCE: 15
tcgtagtcgt cgcgcggaga ata                                           23

<210> SEQ ID NO 16
<211> LENGTH: 23
<212> TYPE: DNA
<213> ORGANISM: artificial sequence
<220> FEATURE:
<223> OTHER INFORMATION: probe ITGA4

<400> SEQUENCE: 16
ttcgatcggt cgtttttata acg                                           23

<210> SEQ ID NO 17
<211> LENGTH: 28
<212> TYPE: DNA
<213> ORGANISM: artificial sequence
<220> FEATURE:
<223> OTHER INFORMATION: probe RXFP3

<400> SEQUENCE: 17
gcgttttggg attacgtatg tttttgg                                       28

<210> SEQ ID NO 18
<211> LENGTH: 27
<212> TYPE: DNA
<213> ORGANISM: artificial sequence
<220> FEATURE:
<223> OTHER INFORMATION: probe ZNF671

<400> SEQUENCE: 18
cgtgggcgcg gacagttgtc gggagcg                                       27
```

```
<210> SEQ ID NO 19
<211> LENGTH: 25
<212> TYPE: DNA
<213> ORGANISM: artificial sequence
<220> FEATURE:
<223> OTHER INFORMATION: primer HPV_F

<400> SEQUENCE: 19
ggttataata atggtatttg ttggg                                       25

<210> SEQ ID NO 20
<211> LENGTH: 27
<212> TYPE: DNA
<213> ORGANISM: artificial sequence
<220> FEATURE:
<223> OTHER INFORMATION: primer HPV_R

<400> SEQUENCE: 20
taaaaaataa actataaatc atattcc                                     27
```

METHOD FOR EARLY DIAGNOSIS OF CARCINOMAS OF THE ANOGENITAL TRACT

CROSS REFERENCE TO RELATED APPLICATION

The present invention is a national stage application of PCT EP2010/005735, filed Sep. 17, 2010, which claims priority to EP application No. 09011941.3, filed Sep. 18, 2009 which are hereby incorporated by reference in their entireties.

The present invention relates to a method for the early diagnosis of carcinomas of the anogenital tract, preferably of the cervical carcinoma, and the preliminary stages thereof. The method is based on the determination of the methylation status of segments of the gene regions of ASTNI (astrotactin 1) and ZNF671 (zinc finger protein 671, transcription factor). A DNA methylation in regions rich in guanine/cytosine, the so-called CpG islands, in the promoter region and/or the 5'-region of at least one of these genes or of both genes is characteristic of carcinomas or preliminary stages of carcinomas of the anogenital tract. The detection of correspondingly modified DNA is utilized diagnostically. The present invention also relates to kits which permit the conduction of the diagnostic method according to the invention.

Cancer of the cervix uteri (cervical carcinoma) is the second most frequent malignant cancerous disease in women world-wide. It develops in the course of an infection with so-called high-risk human papilloma viruses (hr-HPV) via preliminary stages which are referred to as cervical intraepithelial neoplasias (eIN). CIN1: (light dysplasia) ranges from basal to at most one third of the height of the epithelium; CIN2: (moderate dysplasia) up to two thirds of the epithelium; CIN3: (high-grade dysplasia) penetrates almost the entire epithelium. CIN2 and CIN3 are referred to as severe dysplasias. In connection with the latter dysplasias there is a high risk that they change into a cervical carcinoma. In the present application 1 CIN2, CIN3 and cervical carcinoma are subsumed under the name of CIN2+. Along with an hr-HPV infection further factors are also involved in the cervical carcinogenesis.

The existing preventive test for the detection of a cervical carcinoma and its preliminary stages (CIN) is based on a cytomorphological method (Pap test). The Pap test is highly error prone since some few cells suspected of cancer or CIN must be recognized in a background of thousands of normal cells by means of microscopy. In addition, the evaluation of the cell morphology is extremely subjective. As a result of these weaknesses, the sensitivity of the Pap test 53% for the detection of CIN2+ and the specificity is 96.3% (Cuzick et aL, 2006; Int J Cancer, 119: 1095-1101).

The cancer check-up could be considerably improved by molecular test methods. Since apart from a few exceptions all cervical carcinomas and their preliminary stages contain hr-HPV DNA, HPV-DNA appears to be a model marker for cancer check-up. It was possible to show in various published studies that the HPV-DNA test (a PCR method) has a sensitivity of 96.1% and a specificity of 90.7% for the detection of CIN2+. However, the positive predictive value of an HPV DNA test for CIN2+ which is only 20.3% is poor as expected since many women are only infected with HPV but have no preliminary stages of cancer (Cuzick et al., 2066; Int J Cancer, 119:1095~1101). Thus, there is a need for an improved diagnosis of carcinomas of the anogenital tract 1 in particular of the cervical carcinoma.

It is thus the object of the present invention to provide a method serving the early and reliable diagnosis of carcinomas of the anogenital tract, such as the cervical carcinoma and above all the preliminary stages thereof.

According to the invention this is achieved by the subject matters in the claims.

The present invention is based on Applicant's findings which are described in more detail below as to the correlation between the methylation status of certain genes and the development of carcinomas of the anogenital tract. The CpO islands rich in cytosine/guanine are frequently methylated in the upstream, promoter and promoter-near exon regions of genes in carcinomas and the preliminary stages thereof compared to the corresponding normal tissue. This methylation of genes is not arbitrary but depends on the respective tumor entity (Esteller, 2007, Hum. Mol. Genet., 16: R50-R59). Based on the invention, analyses for methylation were thus carried out with the objective of identifying genes which were particularly often methylated in DNA from smears of female patients having a histopathologically confirmed CIN3 and of female patients having a cervical carcinoma. In addition, the genes in DNA from cervical smears of cytologically inconspicuous but hrHPV-positive women should only be methylated very rarely or not at all. The analysis listed herein shows for the first time that the methylation of certain regions of genes ASTN1 and/or ZNF671 is a valuable marker for the detection of carcinomas of the anogenital tract preferably: CIN2+) in a sample (see FIG. 2). The present invention thus provides improved methods for analyzing a cervical carcinoma and its severe preliminary stages (CIN2+) in a sample (e.g. cell smear of the cervix, cervical flush). Although, as shown by the inventors, the determination of the methylation status of the two above-mentioned genes is already highly significant, it may be helpful for the safeguarding of the diagnosis in medical exceptional cases to also determine the methylation status of one or more further genes, such as DLX1 (distal-less homeobox I, transcription factor), EDIL3 (EGF-like repeats and discoidin I-like domains 3), ITGA4 (a4-integrin) and/or RXFP3 (relaxin/insulin-like family peptide receptor 3).

The present invention is based on the (direct or indirect) detection of the methylation status of ASTNI and ZNF671. It is preferably detected whether the promoter regions of the genes ASTN1 and ZNF671 are hypermethylated. Since methylation usually takes place at promoter regions of genes, methods for the detection of the methylation of the relevant genes usually focus on these regions. However, genes can also be methylated in regions other, than the promoter region since the CpG islands rich in GC are not only found there. The detection of a methylation in such further regions can also be of diagnostic use and is thus also a subject matter of the present invention.

In the present invention! the methylation status of genes ASTNI and ZNF671 is preferably detected in the promoter regions. In this connection, it is examined whether or not certain cytosines are modified, i.e. are methylated, to give 5-methylcytosine. In a DNA from a sample originating from a woman having an hr-HPV infection without detectable clinical changes, the methylation is hardly detectable or not detectable at all in the corresponding positions of the DNA. In women having CIN2+, the probability for a methylation at the selected cytosine residues is, however, high.

Figure 1:
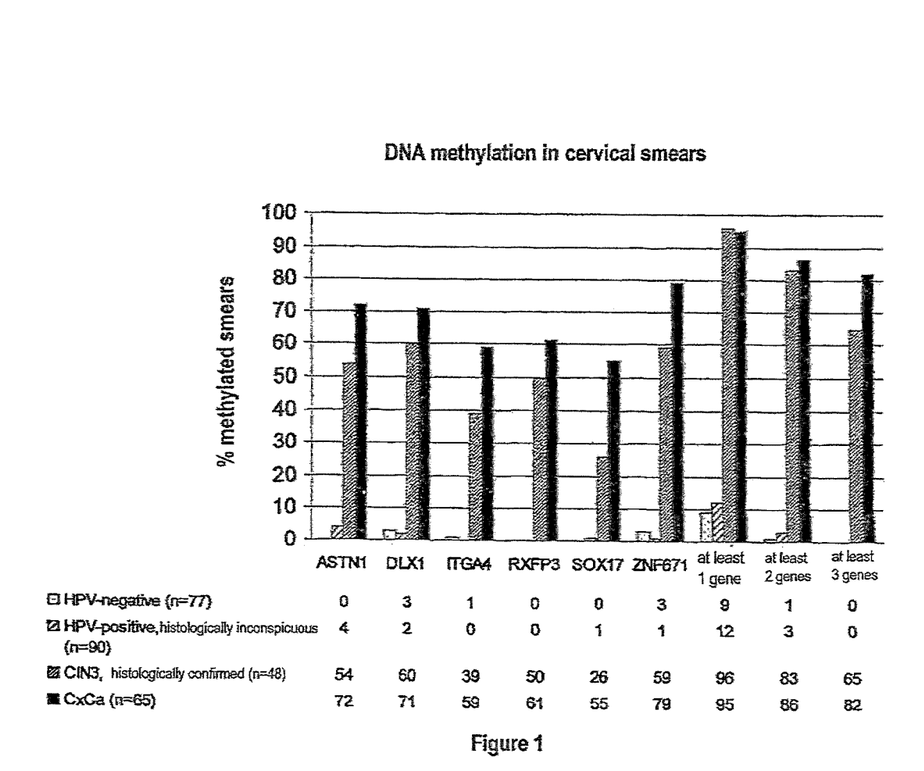
FIG. 1: DNA methylation in various smears
Diagram of the methylation frequency of genes ASTN1, DLX1, EDIL3, ITGA4, RXFP3 and ZNF671 as well as the frequency of the methylation of at least one of the genes each in DNA from smears of Hpv-negative, inconspicuous (n=77), HPVpositive,histopathologically nconspicuous women (n=90), female patients having histopathologically confirmed CIN3 (n=48) and female patients having a cervical carcinoma (n=65).

The specific detection of the methylation of genes, which occurs during the carcinogenesis compared to normal tissue can thus supplement the HPV-DNA detection so as to replace the Pap test. The specificity of the HPV test for the detection of CIW2+ can be considerably improved by methylation analyses carried out in parallel (see FIGS. 1 and 2). The same smear material from the persons to be tested as formerly used for the Pap test and the HPV detection serves as a starting material for the detection of the DNA methylation.

Thus, the present invention relates to a method for detecting anogenital cancer or preliminary stages thereof in a sample, comprising the determination of the methylation status of ASTN1 (astrotactin 1) and ZNF671 (zinc fingerprotein 671), wherein a detectable methylation of one or both genes is indicative of anogenital cancer or a preliminary stage thereof. In the case of inconclusive findings, it is optionally possible to additionally also determine the methylation status of one or more of the genes DLX1 (distal-less homeobox I, transcription factor), EDI13 (EGF-like repeats and discoidin I-like domains 3), ITGA4 (a4-integrin) or RXFP3 (relaxin/insulin-like family peptide receptor 3).

ASTNI (astrotactin 1; accession number NM__004319.1, NM__207108 contained in NC,-OOOOO1.9) is an adhesion protein which plays an important part in the migration of neuronal cells. NF671 (accession number NM__024883, contained in NC__000019.9) is a transcription factor having a typical zinc finger motif. DLX1 (distal-less homeobox 1; accession numbers NM__178120, NM_OOI038493, contained in NC__000002.11) is a transcription factor and influences the cell differentiation. EDIL3 (EGF-like repeats and discoidin I-like domains 3; accession number NM__005711, contained in NC__000005.8) is an integrin ligand and plays an important part in angiogenesis. It might be important for the restructuring and development of vessel walls. In addition, EDIL3 promotes the adhesion of endothelial cells. ITGA4 (a-4 integrin; accession number NM__000885, contained in NC__000002.10) belongs to the family of a-integrins which together with one 1S-integrin each occur as integral membrane proteins. They serve as receptors for fibronectin and thus play an important part in cell adhesion. RXFP3 (relaxin/insulin-like family peptide receptor 3; accession number NM 016568, contained in NC 000005.8) serves as a G-~, ~ protein-linked receptor for relaxin 3.

The expression "anogenital cancer" used herein comprises all cancer types of the anogenital tracts, i.e. in the genital, perineal, anal and perianal regions. These types are preferably cervical carcinoma, vulvar cancer, ovarial carcinoma and endometrial carcinoma.

The expression "preliminary stages" used therein refers to severe preliminary stages and comprises CIN2 and CIN3. The term "sample" used herein comprises any body samples where DNA methylation can be detected. Examples of such body samples are blood, smears, sputum, urine, stool, liquor, bile, gastrointestinal secretions, lymph fluid, bone marrow, organ aspirates and biopsies. In particular, smears and biopsies are useful when the detection of anogenital carcinomas, e.g. cervical carcinomas, is concerned. A person skilled in the art knows suitable methods and auxiliary agents for sampling. The person skilled in the art also knows methods and reagents for the DNA isolation from the sample, e.g. extraction with phenol/chloroform or by means of commercial kits.

The expression "methylation status" used herein refers to the hypermethylation of the genomic DNA in the region of the primex' binding sites of the corresponding genes, preferably in CpG islands rich in GC in the 5'- and promoter regions.

In a preferred embodiment, the diagnostic method according to the invention is used for the diagnosis of cancer of the cervix uteri (cervix carcinoma) and its preliminary stages (together CIN2+).

The method according to the invention determines the methylation of the genes ASTN1 and ZNF671. The term "methylation" used herein is synonymous with the term "hypermethylation" common in molecular biology. It refers to the methylation differing from the normal state within a DNA segment rich in generally guanine and cytosine and in particular CG-dinucleotides, a so-called CpG island.

The sample used for the method according to the invention is preferably a cervical smear which provides very reliable results.

The methylation status of the promoter region and of the 5' and promoter-near exon regions of a gene are determined in another preferred embodiment of the method according to the invention. These regions are particularly informative.

The methylation of DNA is preferably detected after a preceding modification of non-methylated cytosines by the bisulfite method by means of what is called a methylation-specific PCR (MSP) using suitable primer pairs. In the bisulfite method, unmethylated cytosines are converted into uracil, methylated cytosines (5-methylcytosine) are protected against this conversion. Uracil usually has pairing properties differing from cytosine, i.e. it behaves like thymine. MSP is an established technique for the detection of DNA methylation. MSP is based on primers and possibly probes which permit a distinction between methylated and unmethylated DNA, i.e. the formation of an amplification product shows a methylation, thus corresponding to a positive finding.

The design of the primers for the detection of the methylation status depends on the localization and sequence of the methylation regions of ASTN1 and ZNF671 as well as on the methylation regions of DLX1, EDIL3, ITGA4 and/or RXFP3 if the methylation status of these genes shall also be determined, where appropriate.

The methylation-specific primers for ASTN1 and ZNF671 usable in this invention bind during the test method only to the bisulfate-modified sample DNA if it was methylated to certain cytosines within the primer binding sites. If these regions were not methylated before the bisulfate treatment, the primers do not bind and no reaction, product is formed. For example, the presence of a reaction product refers to methylation of the DNA region of the particular gene and thus to the possible presence of e.g. CIN2+ in the case of DNA from cervical smears.

A real-time PCR method (QMSP) which does not only permit a qualitative detection of the methylation but also a quantification of the methylated DNA segments is particularly preferred. This MSP can be carried out in a fluorescence-based real-time method where the formation of the methylation-specific product is pursued by the incorporation of a fluorescent dye, e.g. SYBR-Green. The methylation of marker genes can be detected by these two methods (MS and QMSP) in a high background of non-methylated DNA (Shames et al., 2007, Cancer Lett. 251:187-98). PCR based methods can also be used in high-throughput methods and are thus also particularly suited for cancer check-up.

Even more preferred is a QMSP based on the "MethyLight" technique, fluorescent probes being used for the respective gene segments to be tested for methylation. The probe carries the fluorescent dye at the 5'-end and a quencher at the 3'-end. It binds to the PCR reaction product between the two specific primers. Fluorescent dye is released as soon as the probe is decomposed after binding to the target sequence by the 5'-3'-exonuclease activity of the DNA polymerase. The measured fluorescence reflects the amount of product formed. The number of reactions to be carried out can be correspondingly reduced for samples to be investigated in this method by using several oligonucleotides and probes (Shames et al., 2007, Cancer Lett. 251:187-98). Suitable fluorescent dyes and quenchers are known to the person skilled in the art, e.g. as fluorophore FAM, HEX™, NED™, ROX™, Texas Red™, etc., and as quenchers TAMRA or BHQ.

In a particularly preferred embodiment, the method of the present invention is carried out as a multiplex experiment. Such a multiplex experiment permits the detection of e.g. CIN2+ by the analysis of the methylation status of several genes, which is known to be correlated with the presence of CIN2+, in a single assay per sample. The multiplex method offers several advantages since the methylation status of the gene set to be tested can be determined in one or two reactions per sample. This saves considerable time, sample material and material costs. In the multiplex experiment, the methylation-specific primers are used for up to five genes to be tested. In addition, one further specific oligonucleotide each, what is called a probe, is used for every gene. This probe carries at one end a fluorescent dye and is modified such that the fluorescence does not occur until the probe binds specifically to the reaction products forming during the experiment. The probes carry different fluorescent groups and therefore all can be detected simultaneously. The method according to the invention can so be carried out by means of the "microarray" technology.

The person skilled in the art knows further methods for determining the methylation status, e.g. those based on a direct determination of the amount of specific product by fluorescence. For example, the molecular beacon technology can also be used for the diagnostic method according to the invention. Molecular beacons are oligonucleotides which are linked to both a reporter fluorophore and a quencher. The nucleotides at the 5'-end of the probe are complementary to those at the 3'-end so as to form a secondary structure characteristic of molecular beacons. In this state which is referred to as a hair-needle structure, the reporter shows no fluorescence due to its minor distance to the quencher. The distance between quencher and reporter is increased as a result of the attachment of the loop region to the complementary DNA sequence between the primers during a PCR cycle. The reporter fluorescence can thus be observed.

Another technique suitable for carrying out the method according to the invention is the "scorpion" technology. Scorpion probes are complex oligonucleotides which combine the properties of real-time PCR probes and PCR primers in one (single-scorpion) or two molecules (bi-scorpion). Similar to the molecular beacons, they include a characteristic secondary structure having a self complementary shaft region whose ends were modified with a reporter fluorophore and a quencher. In addition, these probes carry a PCR primer at the 3'-end. During a PCR cycle, reporter fluorescence can be observed by the attachment of the loop region to a complementary DNA sequence and thus an increased distance between quencher and reporter when the DNA concentration increases. For the detection of the binding of the different probes the latter are coupled with fluorescent dye molecules.

Furthermore, positive and/or negative control genes, e.g. an unmethylated control gene, can be co-amplified when the method according to the invention is carried out.

It is known that the methylation of genes is often connected with a transcription blockade and thus a lacking translation. Thus, the method according to the invention also comprises the indirect determination of the methylation status by determining the concentration of the corresponding RNA and/or protein. The detection thereof can be done by common methods/e.g. (for RNA) via Northern blot analysis, RT-PCR, etc., and (for proteins) via antibody-based methods or methods which are based on the determination of a biological activity of the protein.

The method according to the invention can be based on the following steps, for example:
(a) DNA is isolated according to a standard method from a cell smear of the person to be tested/e.g. QiaAmp DNA-Mini kit, according to the instructions of the manufacturer (QIAGEN, Hilden, Germany);
(b) In a second step, it is preferably investigated whether the sample to be analyzed contains hr-HPV-DNA. This detection is done with an already established method such as the GP5+/6+ PCR EIA method (Jacobs et al./1995 J Clin Microbial 33:901-905). All hr-HPV types (HPV16, 18, 26, 31, 33, 35, 39/45, 51, 52, 53, 56/58, 59, 66, 68, '73, 82) should be covered. The detection of a house-keeping gene, e.g. β-globin or β-actin ensures that a sufficient amount of DNA of sufficient quality/which can also be amplified, is available in the sample;
(c) In an HPV-negative sample, the presence of a CIN2+ is almost 100% excluded (Cuzick et al., 2006; Int. J. Cancer, 119:1095-1101). Therefore, these samples need not be further investigated. The differentiation between women having an hr-HPV-positive finding either with or without CIN2+ is then done via the determination of the methylation status of the genes ASTN1 and ZNF671;
(d) For this purpose, the DNA of the hr-HPV-positive samples is chemically converted according to the bisulfate method, e.g. by means of a commercial kit (e.g. Methylation Gold Kit, Zymo Research, Orange, Calif., U.S.A.). Here, all nonmethylated cytosines of the DNA sample are converted into uracils by treatment with sodium bisulfate and subsequent alkaline hydrolysis;
(e) The relevant DNA is amplified and analyzed by means of specific primers for the methylated form of the respective genome segments by PCR;
(f) For the detection of the methylation of the genes ASTN1 and ZNF671 in a methylation-specific PCR or QMSP, the following methylation-specific primers can be used:

```
ASTN1_F        CGTAAGCGTTGTTAGCGTAGC
               (SEQ ID No.: 1)

ASTN1_R        CGCGAAATCGAAACGAAAACG
               (SEQ ID No.: 2)

ASTN1_F        CGGAGGACGTAGTATTTATTCGC
               (SEQ ID No.: 11)

ASTN1_R        CTACGTCCCCGATCGAAACG
               (SEQ ID No.: 12)
```

However, the diagnostic method according to the invention is not limited to the use of these primers for the detection of the methylation of genes ASTN1 and ZNF671. It also comprises primers of other sequences which can serve for detecting the methylation of both genes.

(g) For the detection of the methylation of genes ASTN1 and ZNF671 by MethyLight analysis, fluorescent probes are used in addition to the above described primers:

```
ASTN1       GTAATTCGTTTGTTTCGTAAGTTGTTCG
            (SEQ ID No.: 13)

ZNF671      CGTGGGCGCGGACAGTTGTCGGGAGCG
            (SEQ ID No.: 18)
```

Depending on the application, the probes are coupled with the corresponding fluorescent dyes. However, the invention is not limited to the use of these probes for the detection of the methylation of genes ASTN1 and ZNF671. It also comprises probes having other sequences which may serve for detecting the methylation of both genes.

A quantification of the methylation of the marker genes is not compulsory. What is decisive is that e.g. by MSP or QMSP at least one cell with methylated marker gene(s) can be detected in a background of 1000 cells without methylated marker gene(s).

In a further particularly preferred embodiment of the method according to the invention the HPV-DNA is additionally quantified in the sample. This enables an assessment of the number of HPV-positive cells in the DNA modified by bisulfite treatment by PCR with hr-HPV-specific oligonucleotide primers adapted correspondingly to the bisulfite modification. The primers preferably permit the amplification in the conserved L1 region of the HPV genome and can comprise the following sequences, for example:

```
HPV-F       GGTTATAATAATGGTATTTGTTGGG
            (SEQ ID No.: 19)

HPV_R       TAAAAAATAAACTATAAATCATATTCC
            (SEQ ID No.: 20)
```

In a further preferred embodiment, the methylation of one or more of the genes DLX1, EDIL3, ITGA4 and/or RXFP3 is checked. Primers usable for this purpose are:

```
DLX1_F      TATCGGGATTCGCGTTTGTAC
            (SEQ ID No.: 3)

DLX1_R      CGACCGAACTAAAACTCAACTCG
            (SEQ ID No.: 4)

EDIL3_F     GTTTTCGGCGGTTCGTTC
            (SEQ ID No.: 5)

EDIL3_R     CGAACGCTCGACTATCGC
            (SEQ ID No.: 6)

ITGA4_F     CGAATTCGGTTTTCGAAGGGTC
            (SEQ ID No.: 7)

ITGA4_R     CACGACCGAATAACCGAACAAC
            (SEQ ID No.: 8)

RXFP3_F     ATTTCGGAAAGCGTTTTTCGC
            (SEQ ID No.: 9)

RXRP3_R     CTACGTCTCTCCGCGATTATC
            (SEQ ID No.: 10)
```

In order to detect the methylation of genes DLX1, EDIL3, ITGA4 and RXFP3 by MethyLight analysis, fluorescent probes are used in addition to the above described primers:

```
DLX1        CGTAAACGTTAGCTGTTCTGGAAACCG
            (SEQ ID No.: 14)

EDIL3       TCGTAGTCGTCGCGCGGAGAATA
            (SEQ ID No.: 15)

ITGA4       TTCGATCGGTCGTTTTTATAACG
            (SEQ ID No.: 16)

RXFP3       GCGTTTTGGGATTACGTATGTTTTTTGG
            (SEQ ID No.: 17)
```

Depending on the application, the probes are coupled to corresponding fluorescent dyes.

A further subject matter of the present invention is a kit for carrying out a method according to the invention. Such a kit comprises gene-specific primers or primer pairs for determining the methylation status of ASTN1 (astrotactin 1) and ZNP671 (zinc finger protein, transcription factor), preferably the primers and/or primer pairs defined in more detail above. In a further embodiment, the kit can additionally contain gene-specific primers or primer pairs to determine the methylation status of DLX1 (distal-less homeobox 1), EDIL3 (BGP-like repeats and discoidin I-like domains 3), ITGA4 (a4-integrin) and/or RXFP3(relaxin/insulin-like family peptide receptor 3), preferably the primers and/or primer pairs which are defined in more detail above.

The kit can additionally also contain a probe as described in more detail above and/or a primer pair for the detection of an HPV infection. Finally, the kit can additionally contain at least one of the following constituents in separate containers:

(a) reagents for the isolation of DNA;

(b) enzyme for DNA amplification;

(c) sodium bisulfate;

(d) one or more buffers.

One or more representatives of the individual components of the kit can be available.

It is thus possible with the present invention to diagnose carcinomas of the anogenital tract, in particular cervical carcinomas, at an early stage. In particular, preliminary stages of these carcinomas can be detected early. It must be pointed out that a distinction can be made between hr-HPV positive women with or without clinically relevant tissue modification, e.g. CIN2+. Another characterizing factor is that the results obtained by a method according to the invention are not subject to a subjective assessment and therefore the false-negative or false-positive results of a pap test can be avoided, for example. In addition the present diagnostic method according to the invention distinguishes itself by a rapid and simple handling and therefore it is suited for large screening measures, in particular also in third world countries. Thus, the present invention makes an important contribution to the modern diagnosis of anogenital cancer, in particular cervical carcinoma, or preliminary stages thereof.

In this respect, it should be noted that as a result of the inventive combination of determining the methylation status of ASTN1 and ZNF671 a superior diagnostic confirmation with respect to the detection of CIN2+ lesions can be achieved, which exceeds the individual determination of other genes. For example RXFP3 (Huang et al.) is a marker which is more than 10% worse than ASTN1 and ZNF671 (see FIG. 1). The above mentioned additional determination of the methylation status of the further marker genes is thus only necessary in exceptional cases and is only used according to the invention to confirm the diagnosis.

The invention is explained by the following example

EXAMPLE 1

DNA Methylation in Smears (1) Smears of 77 HPV-negative women, (2) smears of 90 hr-HPV-positive women where there was no indication (histopathologically) of a tissue change; (3) smears of 48 hr-HPV-positive women having a histopathologically confirmed CIN3, and (4) smears of 65 hr-HPV-positive women having a histopathologically confirmed cervical carcinoma were investigated.

Figure 2:
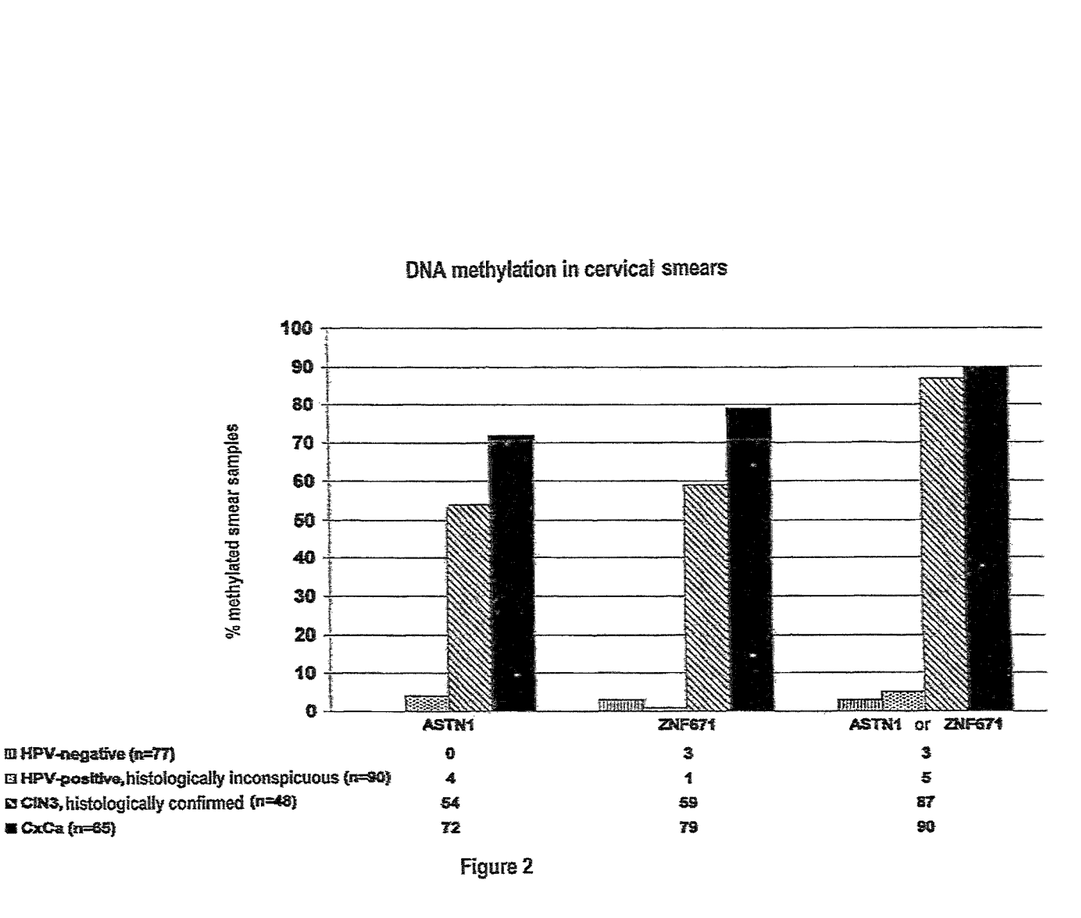
FIG. 2: DNA methylation in various smears
Diagram of the methylation frequency of the genes ASTN1 and ZNF671 as well as the frequency of the methylation of at least one of the genes each in DNA from smears of HPVnegative inconspicuous women (n=77), HPV-positive, histopathologically inconspicuous women (n=90), female patients with histopathologically confirmed CrN3 (n'"48) and female patients having a cervical carcinoma (n=65).

The results are shown in FIG. 2. FIG. 2 shows the methylation frequency of the genes ASTN1 and ZNF671 in the individual groups. A methylation of at least one of the genes occurred in 87% of the CIN3 samples and 90% of the cervical carcinoma samples but only in 3% of the hr-HPV negative and 5% of the hr-HPV-positive women without tissue changes. As a result of the combination of the two genes, it is thus possible to obtain an almost 100% diagnostic confirmation. This shows the reliability of the method according to the invention.

The PCR for the detection of both an HPV infection and for the detection of the methylated genes is very sensitive. The present example is based on the respective qualitative determination of the HFV status and the methylation status of the marker genes. By a quantitative determination of the HFV DNA, a limiting value can be defined which corresponds to a minimum number of HFV-positive cells in the sample. As a result, the specificity of the methylation-specific PCR can be further increased for the detection of CIN2+.

The invention claimed is:

1. A method for detecting anogenital cancer or preliminary stages thereof in a sample, comprising determining the methylation status of ASTN1 (astrotactin 1) and ZNF671 (zinc finger protein, transcription factor), wherein ASTN1 and/or ZNF671 are methylated in a positive sample, and wherein primer pairs are used which comprise the following sequences:

```
(a)     CGTAAGCGTTGTTAGCGTAGC    (ASTN1_F)
        (SEQ ID No.: 1)
        and CGCGAAATCGAAACGAAAACG    (ASTN1_R);
        (SEQ ID No.: 2)

(b)     CGGAGGACGTAGTATTTATTCGC  (ZNF671_F)
        (SEQ ID No.: 11)
        and CTACGTCCCCGATCGAAACG     (ZNF671_R).
        (SEQ ID No.: 12)
```

2. The method according to claim 1, wherein at least one probe is used which comprises one of the following sequences:

```
(a)     GTAATTCGTTTGTTTCGTAAGTTGTTCG  (ASTN1);
        (SEQ ID No.: 13)

(b)     CGTGGGCGCGGACAGTTGTCGGGAGCG   (ZNF671).
        (SEQ ID No.: 18)
```

3. The method according to claim 1, additionally comprising the detection of HPV.

4. The method according to claim 3, wherein the detection of HPV is via PCR.

5. The method according to claim 4, wherein the HPV is detected using a primer pair comprising the following sequences:

```
(a)     GGTTATAATAATGGTATTTGTTGGG  (HPV_F);
        (SEQ ID No.: 19)
        and (b)     TAAAAAATAAACTATAAATCATATTCC (HPV_R).
        (SEQ ID No.: 20)
```

6. A kit for detecting anogenital cancer or preliminary stages thereof in a sample, comprising: gene specific primer pairs that determine methylation and/or hypermethylation of ASTN1 (astrotactin 1) and ZNF671 (zinc finger protein, transcription factor).

7. The kit according to claim 6, wherein primer pairs are used which comprise the following sequences:

```
(a)
CGTAAGCGTTGTTAGCGTAGC        (SEQ. ID No.: 1)
(ASTN1_F)
and

CGCGAAATCGAAACGAAAACG        (SEQ. ID No.: 2)
(ASTN1_R);

(b)
CGGAGGACGTAGTATTTATTCGC      (SEQ. ID No.: 11)
(ZNF671_F)
and

CTACGTCCCCGATCGAAACG         (SEQ. ID No.: 12)
(ZNF671_R).
```

8. The kit according to claim 6, wherein at least one probe is used which comprises one of the following sequences:

```
(a)
GTAATTCGTTTGTTTCGTAAGTTGTTCG  (SEQ. ID No.: 13)
(ASTN1);

(b)
CGTGGGCGCGGACAGTTGTCGGGAGCG   (SEQ. ID No.: 18)
(ZNF671).
```

9. The kit according to claim 6, additionally containing a primer pair for the detection of HPV.

10. The kit according to claim 9, wherein the HPV is detected using a primer pair comprising the following sequences:

```
(a)
GGTTATAATAATGGTATTTGTTGGG      (SEQ. ID No.: 19)
(HPV_F);
and (b)
TAAAAAATAAACTATAAATCATATTCC    (SEQ. ID No.: 20)
(HPV_R).
```

11. The kit according to claim 6, containing in separate containers additionally at least one of the following constituents:
   (a) reagents for isolating DNA;
   (b) enzyme for DNA amplification;
   (c) sodium bisulfate;
   (d) one or more buffers.

12. The method of claim 1 wherein the anogenital cancer is cancer of the cervix uteri.

13. The method of claim 1 wherein the sample is a cervical smear.

14. The method of claim 1 where the methylation status of the ASTN1 and ZNF671 are determined at the promoter regions.

15. The method of claim 1 wherein the methylation status of the genes is determined by means of methylation-specific PCR (MSP).

16. The method of claim 15 wherein the MSP is a quantitative MSP (QMSP).

17. The method of claim 16 wherein the quantitative MSP is based on the MethyLight technique.

18. The method according to claim 1 wherein the method is a multiplex method.

19. The kit according to claim 7 wherein at least one probe is used which comprises one of the following sequences:

```
(a)
GTAATTCGTTTGTTTCGTAAGTTGTTCG   (SEQ. ID No.: 13)
(ASTN1);

(b)
CGTGGGCGCGGACAGTTGTCGGGAGCG    (SEQ. ID No.: 18)
(ZNF671).
```

20. The kit according to claim 19, additionally containing a primer pair for the detection of HPV and wherein the HPV is detected using a primer pair comprising the following sequences:

```
(c)
GGTTATAATAATGGTATTTGTTGGG      (SEQ. ID No.: 19)
(HPV_F);
and (d)
TAAAAAATAAACTATAAATCATATTCC    (SEQ. ID No.: 20)
(HPV_R).
```

* * * * *